United States Patent
Tabaru et al.

(10) Patent No.: US 9,851,292 B2
(45) Date of Patent: Dec. 26, 2017

(54) PARTICLE DETECTION DEVICE

(71) Applicant: Fuji Electric Co., Ltd., Kanagawa (JP)

(72) Inventors: Masaya Tabaru, Tokyo (JP); Naoki Takeda, Kanagawa (JP); Kazuhiro Koizumi, Kanagawa (JP); Noritomo Hirayama, Tokyo (JP)

(73) Assignee: FUJI ELECTRIC CO., LTD., Kanagawa (JP)

( * ) Notice: Subject to any disclaimer, the term of this patent is extended or adjusted under 35 U.S.C. 154(b) by 0 days.

(21) Appl. No.: 15/177,593

(22) Filed: Jun. 9, 2016

(65) Prior Publication Data

US 2017/0016820 A1   Jan. 19, 2017

(30) Foreign Application Priority Data

Jul. 15, 2015 (JP) .................. 2015-141328

(51) Int. Cl.
   *G01N 15/14* (2006.01)
   *G01N 21/71* (2006.01)
   *G01N 15/00* (2006.01)

(52) U.S. Cl.
   CPC ..... *G01N 15/1459* (2013.01); *G01N 15/1429* (2013.01); *G01N 21/71* (2013.01); *G01N 2015/0046* (2013.01); *G01N 2015/1486* (2013.01); *G01N 2015/1493* (2013.01)

(58) Field of Classification Search
   CPC .................................................. G01N 21/47
   USPC ....................................................... 356/338
   See application file for complete search history.

(56) References Cited

U.S. PATENT DOCUMENTS

| 4,135,815 A | * | 1/1979 | Masunaga .............. G02B 7/305 250/201.7 |
| 4,361,825 A | * | 11/1982 | Shockley ................ B60T 17/22 188/151 A |
| 4,571,079 A | * | 2/1986 | Knollenberg .......... G01N 21/53 356/336 |
| 4,798,465 A | * | 1/1989 | Knollenberg ...... G01N 15/0205 356/336 |
| 5,822,104 A | * | 10/1998 | Saito .................... H04B 10/695 330/252 |

(Continued)

FOREIGN PATENT DOCUMENTS

JP  2012-088178 A  5/2012

*Primary Examiner* — Tarifur Chowdhury
*Assistant Examiner* — Omar Nixon
(74) *Attorney, Agent, or Firm* — Chen Yoshimura LLP

(57) ABSTRACT

A particle detection device includes a scattered light detector detecting an intensity of light scattered by a particle irradiated with a laser, an incandescent light detector detecting an intensity of incandescent light from the particle being irradiated with the laser, and a signal processor including: a first peak hold circuit holding a peak in the intensity of the light scattered by the particle; a second peak hold circuit holding a peak in the intensity of the incandescent light from the particle; and a threshold value comparison circuit comparing the peak in the first peak hold circuit to a threshold and, when the peak in the first peak hold circuit exceeds the threshold, outputs a reset signal to the second peak hold circuit immediately thereafter so the peak previously in the second peak hold circuit is reset immediately after the peak in the first peak hold circuit exceeds the threshold.

2 Claims, 13 Drawing Sheets

(56) References Cited

U.S. PATENT DOCUMENTS

| | | | |
|---|---|---|---|
| 5,920,388 A * | 7/1999 | Sandberg | G01N 15/0205 356/315 |
| 2005/0179908 A1* | 8/2005 | Wada | G01P 3/366 356/496 |
| 2006/0120772 A1* | 6/2006 | Kitazawa | G03G 15/0131 399/301 |
| 2014/0022882 A1* | 1/2014 | Sano | G11B 7/0938 369/275.3 |

* cited by examiner

PARTICLE DETECTION DEVICE

BACKGROUND OF THE INVENTION

Technical Field

The present invention relates to a particle detection device for measuring properties such as the number, size, or mass concentration of particles contained in the atmosphere or in the air in a cleanroom, for example.

Background Art

In one well-known class of devices for detecting particles suspended in a gas, sample air that contains the particles is input to the detection device and irradiated with laser light, and then properties such as the number, size, and mass concentration of the particles are measured by detecting the scattered light or incandescent light produced when the particles cross a region that is irradiated with the laser light.

Exhaust gas from diesel engines and exhaust gases produced from burning fuels that are composed primarily of carbon (such as coal, firewood, or biomass fuels, as well as gas produced by forest fires) contains primarily black carbon. When black carbon is momentarily heated by irradiating it with strong laser light such as that in a laser cavity or that from a pulse laser, the black carbon emits incandescent light due to the resulting black-body radiation. Detecting this incandescent light makes it possible to measure the number and size of black carbon particles. This method of detecting the incandescent light produced by black carbon is known as the laser-induced incandescence (LII) method (see Patent Document 1).

FIG. 10 is a block diagram of a signal processor in a conventional particle detection device. As illustrated in FIG. 11, scattered light and incandescent light signals received by a scattered light detector 129 and an incandescent light detector 130 are pulse waves, for example.

The threshold value comparison circuit 133 illustrated in FIG. 10 sets an appropriate threshold value for the received signals, which is used to determine which pulse waves to record. Next, the pulse waves to record are converted from analog values to digital values by AD converters 131 and 132. The digital pulse waves are then input to and recorded on a personal computer (PC) 134 or the like.

However, recording the pulse waves as-is as described above produces an extremely large amount of data, which results in longer signal processing times and a high load on the signal processor. A method such as the following offers a simpler alternative.

FIG. 12 is a block diagram of a signal processor for calculating particle size in a conventional particle detection device. In FIG. 12, components with the same reference characters as components in FIG. 10 are the same components as in FIG. 10. As illustrated in FIG. 12, the peak values of the received pulse waves are held by peak hold circuits 141 and 142. Then, the stored peak values are compared to a threshold value set in a threshold value comparison circuit 145, and the stored peak values that are larger than the threshold value are converted from analog values to digital values by the AD converters 143 and 144.

Here, assume that the peak values to compare are from the scattered light signals. There are two reasons for making this assumption. First, in most cases the particles will always produce scattered light but may not necessarily produce incandescent light. Second, if the scattered light and the incandescent light signals are both used for comparison purposes, then when the particle concentration increases, the amount of time occupied by the AD conversion process while getting the signals increases, which increases the amount of time during which particles cannot be detected (dead time).

Next, the digital scattered light and incandescent light signals are input to a CPU 147, and reset circuits 149 and 150 send reset signals to the respective peak hold circuits 141 and 142. Then the CPU 147 takes the input digital signals and converts the scattered light signals to particle size and the incandescent light signals to black carbon particle size according to peak value-particle size relationships configured in advance in a particle size setting circuit 146. Finally, the calculated particle size values are displayed on a display device 148.

The method described above makes it possible to get just the particle sizes (a small amount of data) from the large amount of data constituted by the original pulse waves, thereby making it possible to shorten processing time and reduce the load on the signal processor.

RELATED ART DOCUMENT

Patent Document

Patent Document 1: Japanese Patent Application Laid-Open Publication No. 2012-88178

SUMMARY OF THE INVENTION

However, the conventional signal processing method described above has the following problems. FIG. 13 is a timing chart illustrating the operation of the signal processor in the conventional particle detection device.

Assume that as illustrated in FIG. 13, during a certain particle detection event, a scattered light signal $S_3$ and an incandescent light signal $S_C$ are obtained (also assume that as illustrated in FIG. 11, the incandescent light is detected slightly after the scattered light). The peak values of the scattered light signal $S_3$ and the incandescent light signal $S_C$ are then respectively held by the peak hold circuits 141 and 142. In this case, because the scattered light signal $S_3$ is not greater than the threshold value, the AD converters 143 and 144 do not perform the AD conversion process. Therefore, as illustrated in FIG. 13, no reset signals are output to the peak hold circuits 141 and 142, and the current peak values $L_3$ and $L_C$ remain stored as-is.

Then, during the next event, a scattered light signal $S_4$ and an incandescent light signal $S_D$ are obtained. In this case, the scattered light signal $S_4$ is greater than the threshold value, and therefore the AD converter 143 converts the associated peak value $L_4$ to a digital signal.

However, because the new incandescent light signal $S_D$ is less than the incandescent light signal $S_C$ from the previous event, the peak vale $L_C$ from the previous incandescent light signal $S_C$ gets converted to a digital signal. As a result, particles that did not produce incandescent light or only produced weak incandescent light are recorded as particles that produced strong incandescent light, and the number of incandescent light-producing particles will be overestimated. Moreover, the scattered light and incandescent light signals no longer correspond uniquely to individual particles, and therefore characteristics of the particle mixture state can no longer be measured.

The present invention was made in view of the above-mentioned problems and aims to provide a particle detection device that maintains a unique correspondence between individual particles and the resulting scattered light and incandescent light signals and does not overestimate the number of particles. Accordingly, the present invention is directed to a scheme that substantially obviates one or more of the problems due to limitations and disadvantages of the related art.

Additional or separate features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve these and other advantages and in accordance with the purpose of the present invention, as embodied and broadly described, in one aspect, the present disclosure provides a particle detection device, including: a scattered light detector that detects an intensity of light scattered by a particle as a result of being irradiated with a laser beam; an incandescent light detector that detects an intensity of incandescent light generated by the particle as a result of being irradiated with the laser beam; and a signal processing part that includes: a first peak hold circuit that holds a peak value in the intensity of the light scattered by the particle detected by the scattered light detector; a second peak hold circuit that holds a peak value in the intensity of the incandescent light generated by the particle detected by the incandescent light detector; and a threshold value comparison circuit that compares the peak value held by the first peak hold circuit to a prescribed threshold value and, when the peak value held by the first peak hold circuit exceeds the prescribed threshold value, outputs a reset signal to the second peak hold circuit immediately thereafter so that the peak value previously held by the second peak hold circuit is reset immediately after the peak value held by the first peak hold circuit exceeds the prescribed threshold value.

The particle detection device of the present invention makes it possible to accurately detect particles even when using a relatively simple signal processing scheme that utilizes peak hold circuits without losing the unique correspondence between individual particles and the resulting scattered light and incandescent light signals and without overestimating the number of particles.

It is to be understood that both the foregoing general description and the following detailed description are exemplary and explanatory, and are intended to provide further explanation of the invention as claimed.

DETAILED DESCRIPTION OF EMBODIMENTS

Next, an embodiment of the present invention (hereinafter, simply "the present embodiment") will be described in detail. Note, however, that the present invention is not limited to the following embodiment, and various modifications may be made without departing from the spirit of the present invention.

Figure 3:
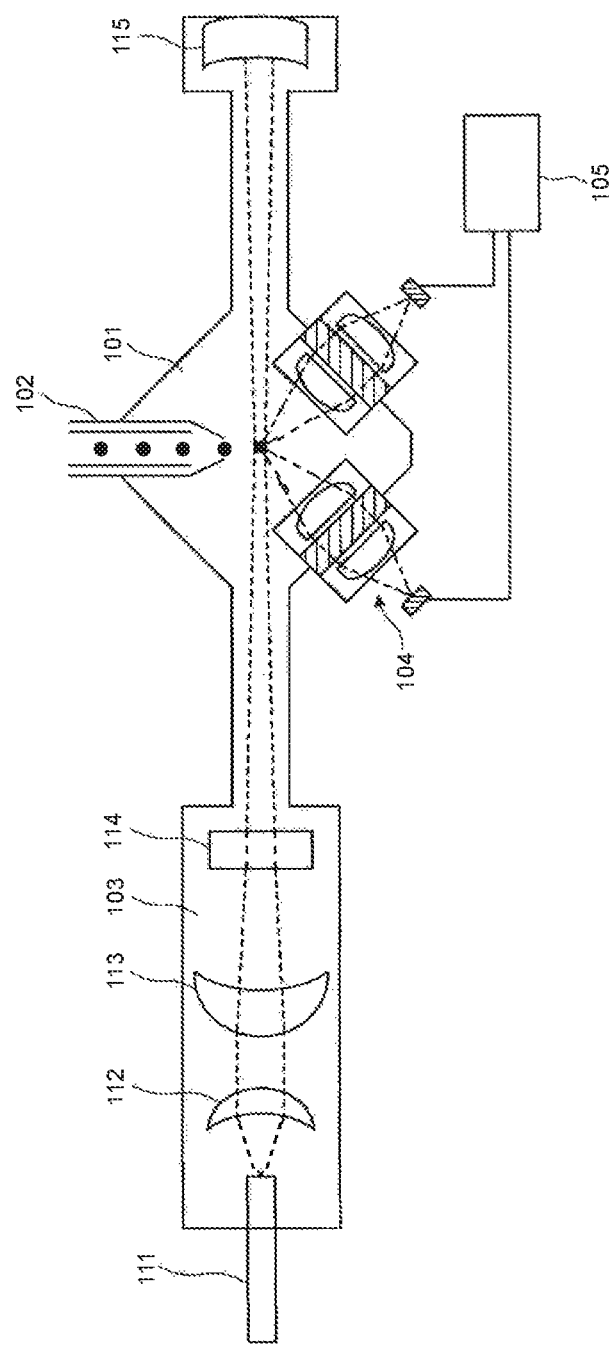
FIG. 3 illustrates the overall configuration of a particle detection device that utilizes the laser-induced incandescence (LII) method.

A signal processor of a particle detection device according to the present embodiment includes a number of characteristic features. However, first the overall configuration of the particle detection device will be described with reference to FIG. 3. FIG. 3 illustrates the overall configuration of the particle detection device, which utilizes the laser-induced incandescence (LII) method.

As illustrated in FIG. 3, this laser-induced incandescence particle detection device includes a detection chamber 101, a particle input unit 102 that inputs particles to the detection chamber 101, a laser emitter 103 (a laser cavity), a detector 104 that detects scattered light and incandescent light, and a signal processor 105 that processes the signals corresponding to the detected light.

Next, each component of the configuration will be described in more detail. First, the particle input unit 102 will be described. In this particle detection device, sample air is irradiated with laser light that is focused to increase the irradiation energy density thereof and thereby make it possible to measure the particles with higher sensitivity. Due to the cross-sectional strength distribution of the laser light, there tends to be a significant difference in the strength of signals from particles that pass through the center region of the laser light and the signals from particles that pass through the peripheral regions of the laser light, even for particles of the same type and shape. To reduce this difference in signal strength, the laser light irradiation region can be expanded, or a particle beam can be formed in order to reduce the size of the region through which the particles cross. Of these methods, the former tends to reduce the power density of the laser light and result in decreased detection sensitivity, and therefore it is preferable that the latter method of forming a particle beam be used.

Figure 4:
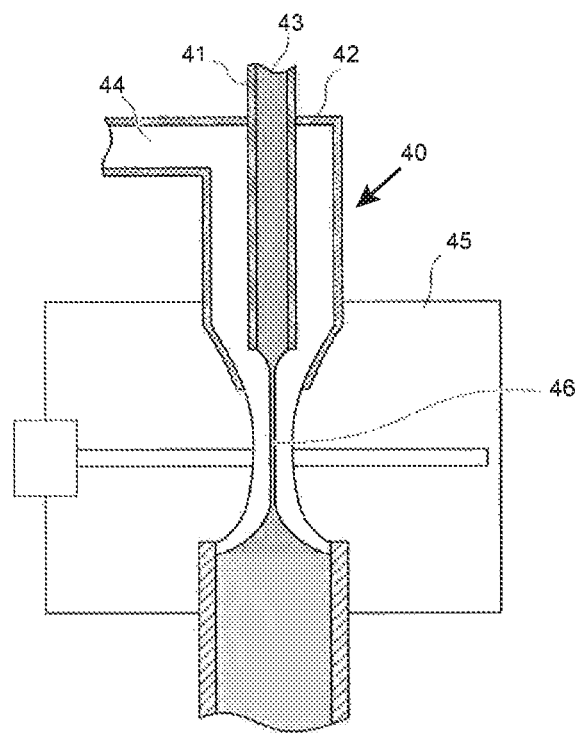
FIG. 4 is an expanded partial view of a particle detection device that includes a particle beam formation unit.

One method of forming a particle beam involves using a sample flow and a sheath flow. FIG. 4 is an expanded partial view of a particle detection device that includes a particle beam formation unit.

As illustrated in FIG. 4, a discharge nozzle (particle beam formation unit) 40 has a dual tube structure that includes an internal nozzle 41 and an external nozzle 42. Sample air 43 is input to the internal nozzle 41, and clean sheath air 44 is input to the external nozzle 42. Enveloping the outermost layer of the sample air 43 with the sheath air 44 and discharging the resulting flow towards a detection chamber 45 at a relatively high velocity of several dozen m/s makes it possible to form a particle beam 46. Moreover, appropriately adjusting the flow rates of the sample air 43 and the sheath air 44 focuses the particle beam 46 to a diameter of approximately 0.1 mm at a position approximately 2 to 5 mm from the discharge nozzle 40, and the particle beam 46 then passes through a prescribed detection region in the detection chamber 45. For example, the flow rate of the sheath air 44 is set to a value approximately 5 to 10 times the flow rate of the sample air 43.

Figure 5:
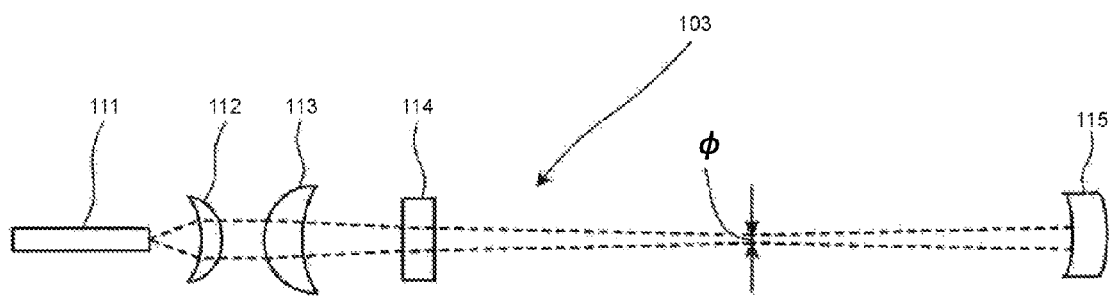
FIG. 5 illustrates the configuration of a laser cavity.

Next, the laser emitter 103 will be described. FIG. 5 illustrates the configuration of the laser cavity. As illustrated in FIGS. 3 and 5, the laser cavity includes a pump laser 111, a collimating lens 112, an imaging lens 113, a laser crystal (such as an Nd:YAG crystal) 114 for converting the wavelength of the laser light, and a high-reflectivity concave mirror (HR mirror) 115.

The pump laser 111 emits laser light with a wavelength of 808 nm, for example, which is then focused by the collimating lens 112, the imaging lens 113, and the laser crystal 114. Moreover, it is preferable that both surfaces of the collimating lens 112 and the imaging lens 113 have an anti-reflective (AR) coating in order to prevent optical feedback to the pump laser 111. The laser crystal 114 converts the focused laser light from a wavelength of 808 nm to a wavelength of 1064 nm. Moreover, an 808 nm AR coating and a 1064 nm high-reflectivity (HR) coating are applied to the surface of the laser crystal 114 through which the 808 nm laser light enters. Furthermore, a 1064 nm AR coating is applied to the surface of the laser crystal 114 that emits the 1064 nm laser light. Together, the 1064 nm HR coating surface of the laser crystal 114 and the high-reflectivity concave mirror 115 form a 1064 nm laser light intracavity. The beam waist of the 1064 nm laser light in the intracavity (the diameter ⌀ illustrated in FIG. 5) is approximately 0.3 mm, for example. Note that the configuration of the laser emitter 103 described above is only an example, and the laser emitter 103 is not limited to this configuration.

Figure 6:
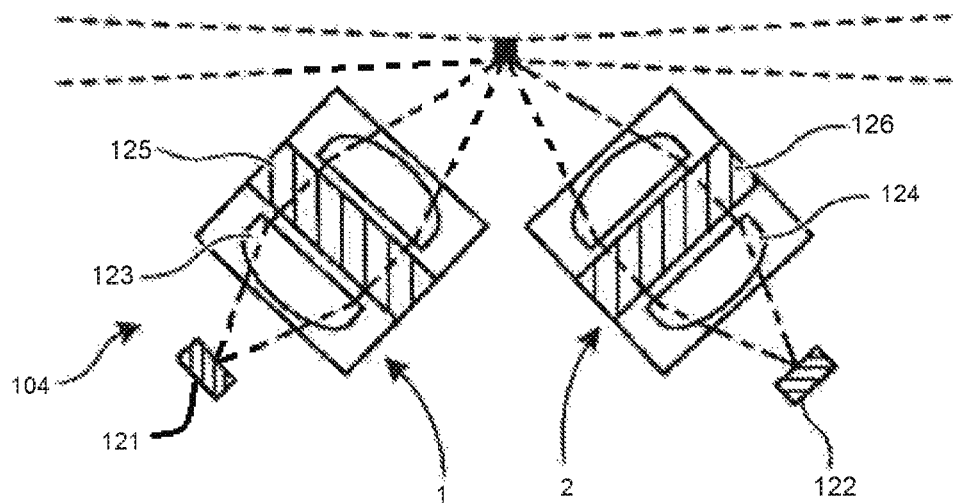
FIG. 6 illustrates the configuration of a detector.

Next, the configuration of the detector 104 will be described. FIG. 6 illustrates the configuration of the detector. As illustrated in FIG. 6, the detector 104 includes an avalanche photodiode (APD) 121, a photomultiplier tube (PMT) 122, lenses 123 and 124, and optical filters 125 and 126, for example. The scattered light from the particles is received by a scattered light detector 1, which includes the lens 123, the optical filter 125, and the APD 121.

Figure 7:
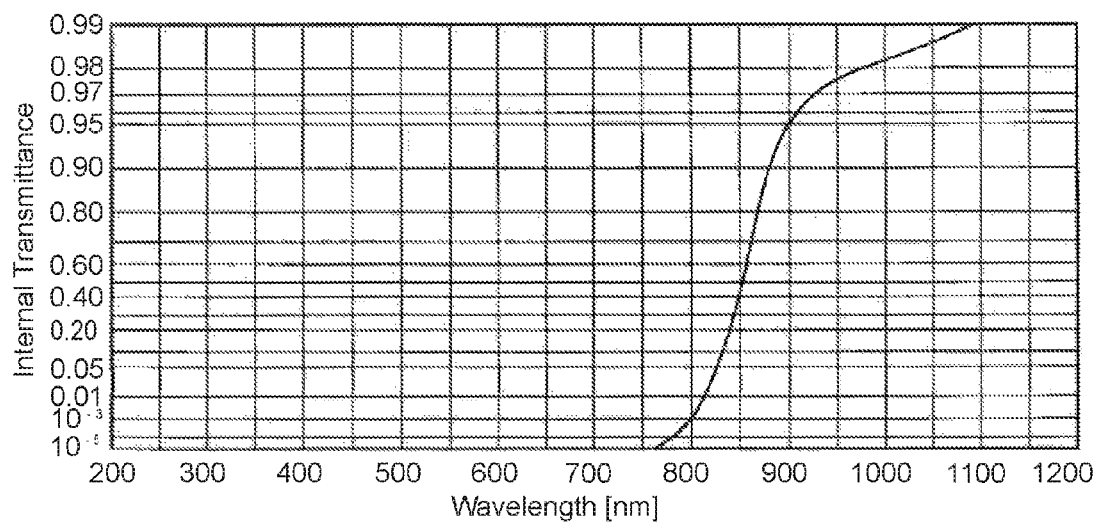
FIG. 7 is a graph showing an example of the passband of an optical filter for detecting scattered light.

The scattered light has the same wavelength as the laser light used to irradiate the particles. Moreover, an optical filter having pass-through characteristics such as those illustrated in FIG. 7, for example, is used for the optical filter 125 so that the scattered light detector 1 does not detect incandescent light. This makes it possible to ensure that the scattered light detector 1 only detects the scattered light.

Figure 8:
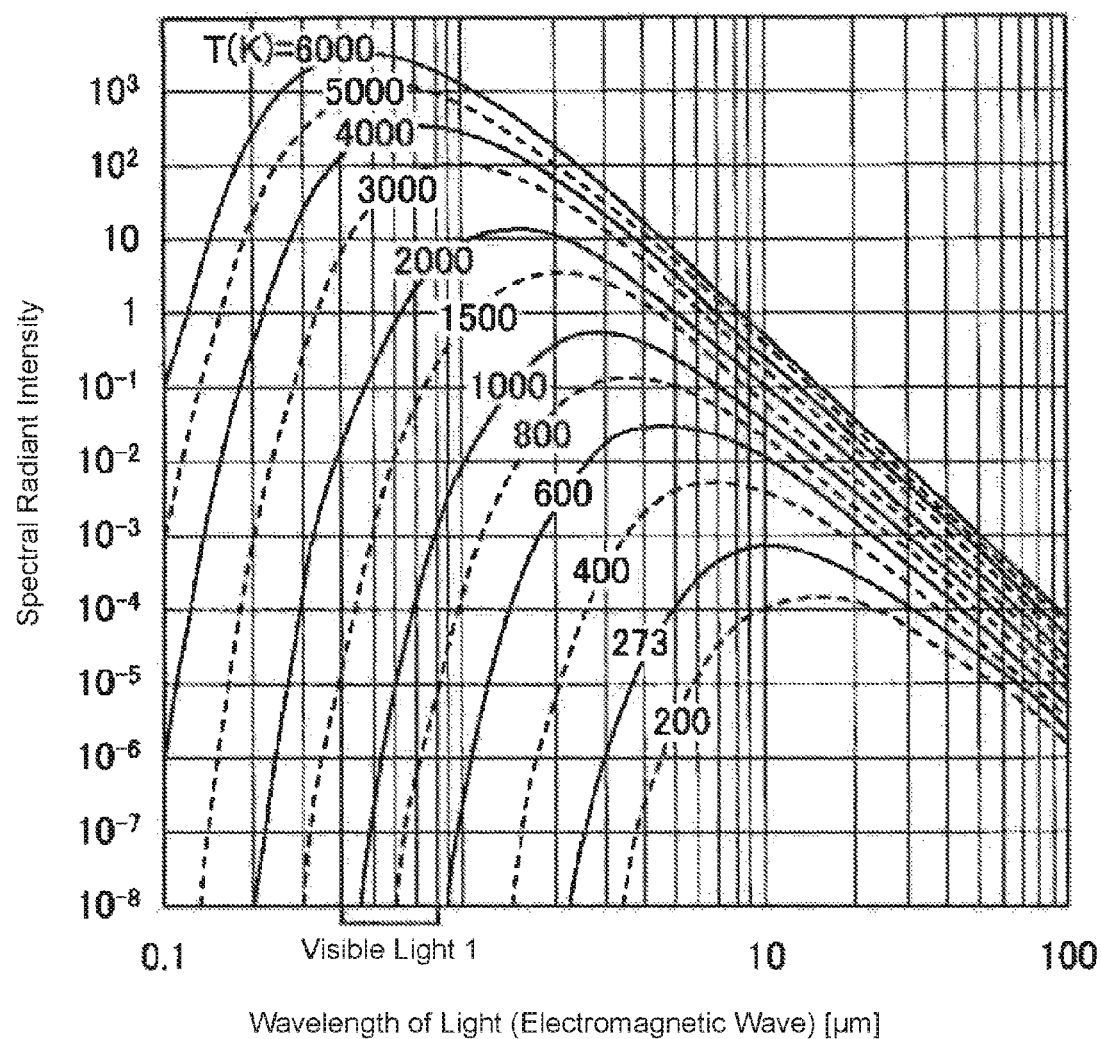
FIG. 8 is a graph showing the relationship between emission wavelength and color temperature.
Figure 9:
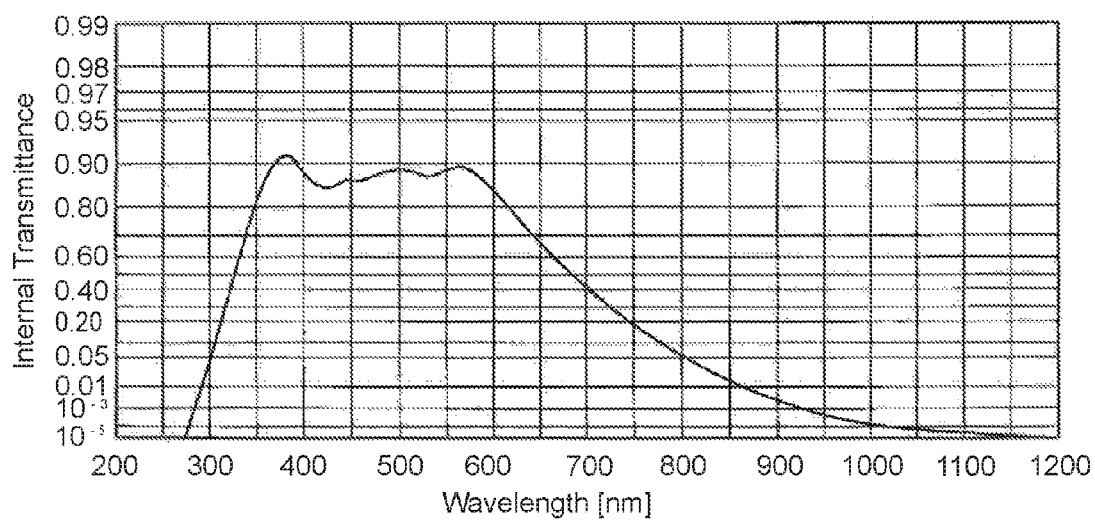
FIG. 9 is a graph showing the passband of an optical filter for detecting incandescent light.
Figure 10:
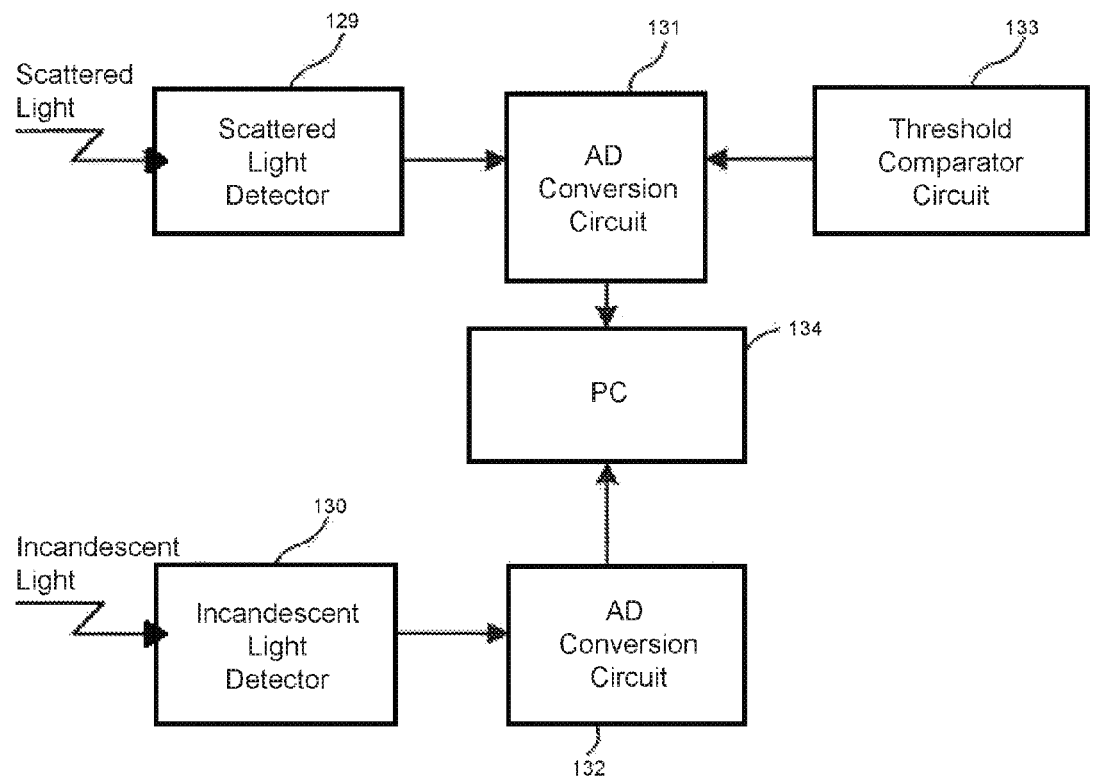
FIG. 10 is a block diagram of a signal processor in a conventional particle detection device.

Furthermore, the incandescent light is received by an incandescent light detector 2, which includes the lens 124, the optical filter 126, and the PMT 122. The incandescent light is black-body radiation (of temperature 4000-5000K), and therefore as illustrated in FIG. 8, the emission wavelengths exhibit a peak near approximately 500 to 600 nm. Therefore, an optical filter with pass-through characteristics such as those illustrated in FIG. 9, for example, is used for the optical filter 126 so that the passband of the optical filter 126 includes the emission wavelengths of the incandescent light but will not pass light of the same wavelength as the laser light.

Figure 1:
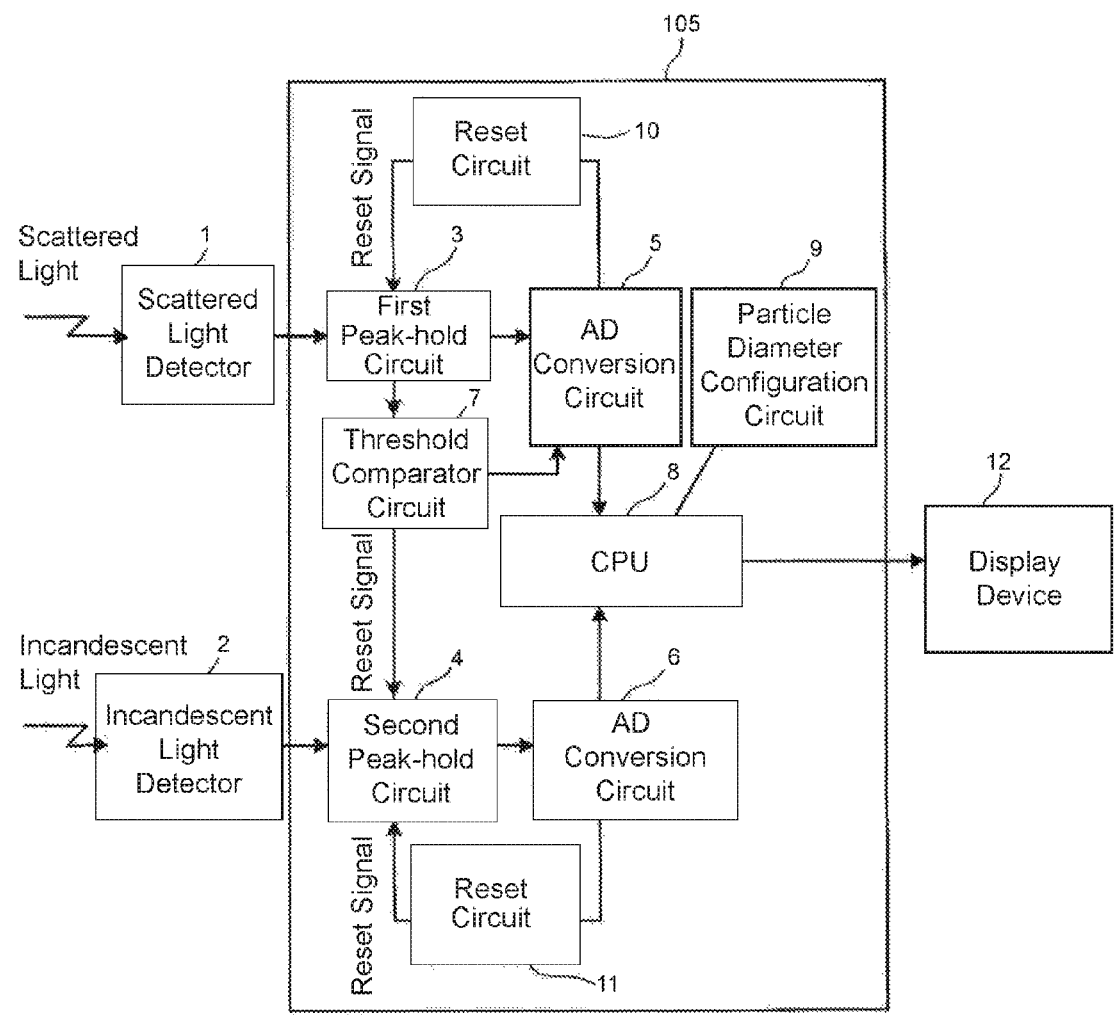
FIG. 1 is a block diagram of a signal processor for a particle detection device according to an embodiment of the present invention.

Next, the signal processor 105 will be described. FIG. 1 is a block diagram of the signal processor of the particle detection device according to the present embodiment.

As illustrated in FIG. 1, the signal processor 105 includes a first peak hold circuit 3, a second peak hold circuit 4, AD converters 5 and 6, a threshold value comparison circuit 7 (threshold comparator circuit), a CPU 8, a particle size setting circuit 9, and reset circuits 10 and 11.

Figure 11:
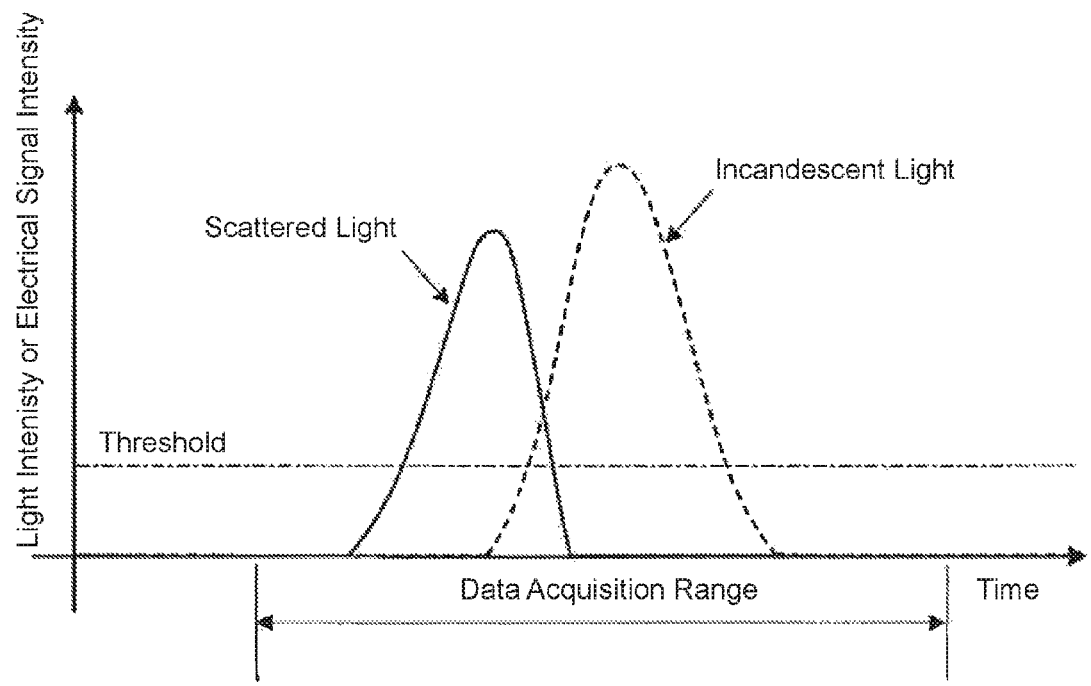
FIG. 11 is a graph showing an example of a scattered light pulse wave and an incandescent light pulse wave.
Figure 12:
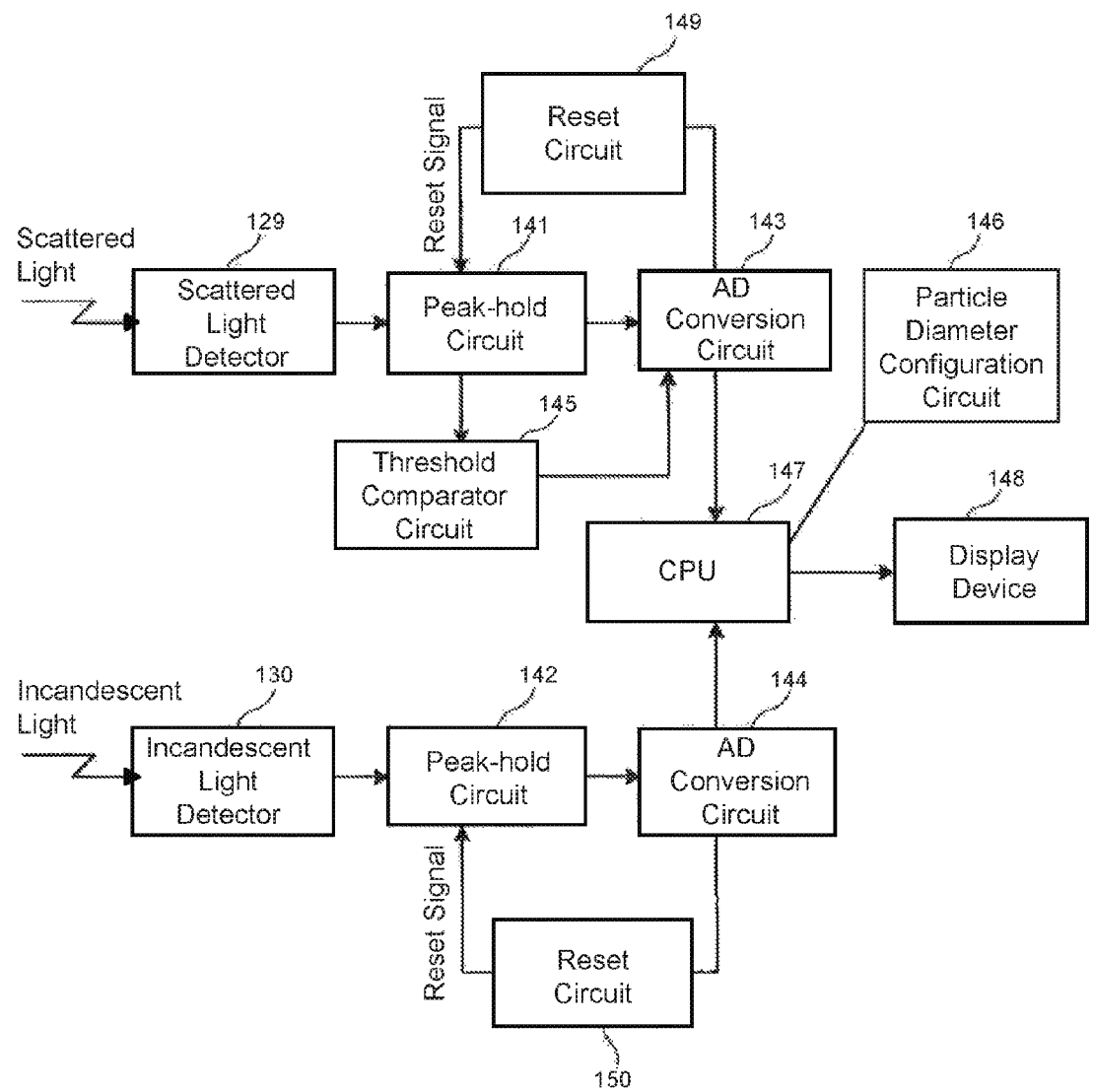
FIG. 12 is a block diagram of a signal processor for calculating particle size in a conventional particle detection device.
Figure 13:
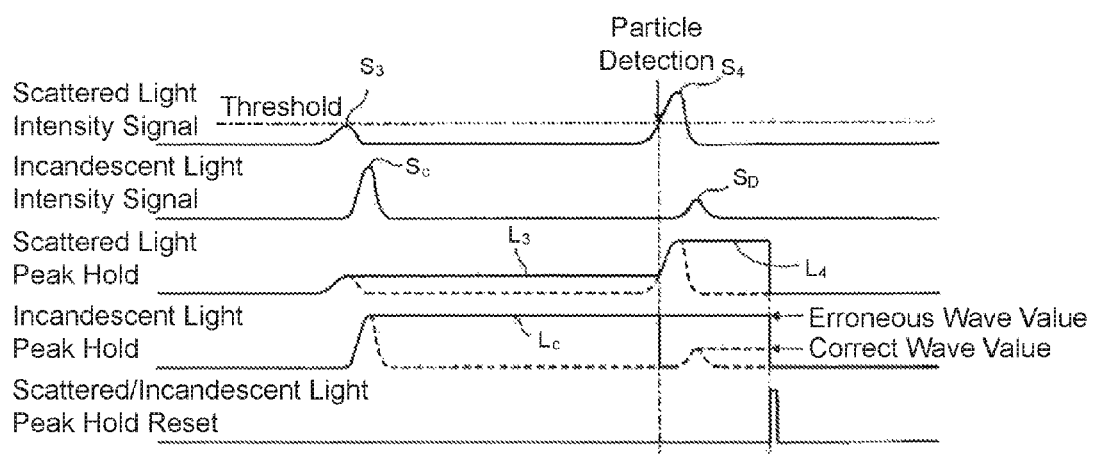
FIG. 13 is a timing chart illustrating the operation of the signal processor in the conventional particle detection device.

As illustrated in FIG. 1, once scattered light is produced, the scattered light detector 1 converts that scattered light to an electrical signal, yielding a scattered light waveform such as that illustrated in FIG. 11. Similarly, the incandescent light detector 2 converts any incandescent light that is produced to an electrical signal, yielding an incandescent light waveform such as that illustrated in FIG. 11. As illustrated in FIG. 11, the incandescent light signal is obtained slightly after the scattered light signal. This is because the incandescent light is produced when black carbon is momentarily heated due to being irradiated with the strong laser light. A non-zero absorption time is required for the black carbon to absorb thermal energy, and therefore the incandescent light is always produced after the scattered light. The present embodiment takes advantage of this fact to improve the configuration of the signal processor 105 in comparison with conventional signal processors.

As illustrated in FIG. 1, the electrical signal from the scattered light detector 1 is sent to the first peak hold circuit 3, and the first peak hold circuit 3 stores the peak value of the intensity of the scattered light as represented by that electrical signal. Similarly, the electrical signal from the incandescent light detector 2 is sent to the second peak hold circuit 4, and the second peak hold circuit 4 stores the peak value of the intensity of the incandescent light as represented by that electrical signal.

Figure 2:
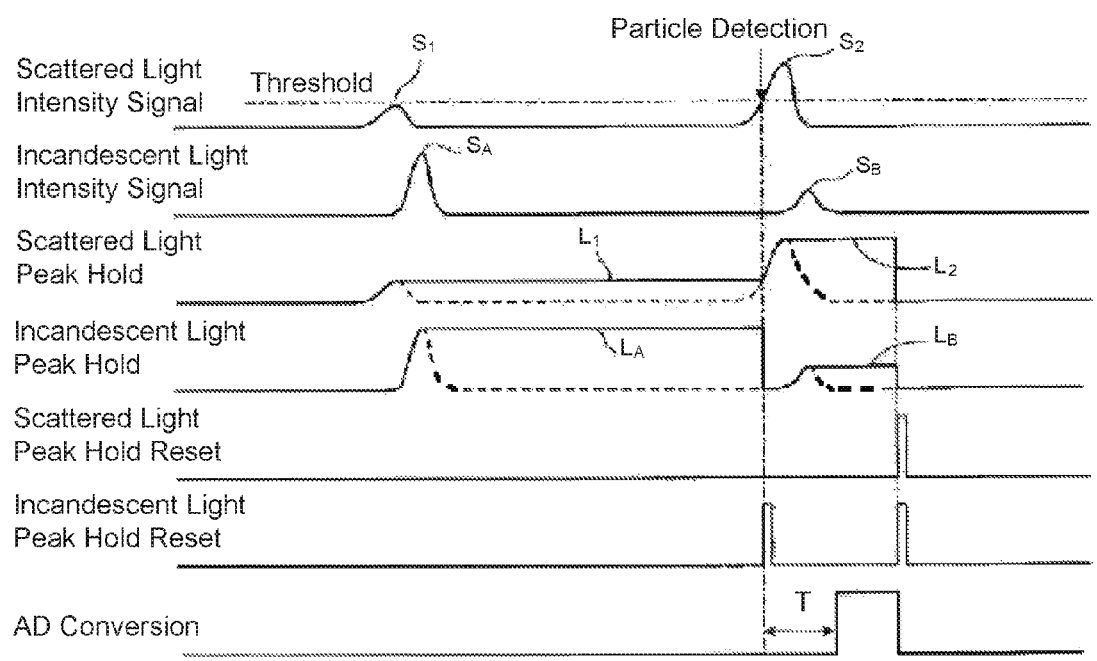
FIG. 2 is a timing chart illustrating the operation of the signal processor in the particle detection device according to the embodiment.

Next, a specific example of the operation of the signal processor will be described with reference to FIGS. 1 and 2. FIG. 2 is a timing chart illustrating the operation of the signal processor in the particle detection device according to the present embodiment.

Assume that as illustrated in FIG. 2, during a certain particle detection event, a scattered light signal $S_1$ and an incandescent light signal $S_A$ are obtained. The peak values of the scattered light signal $S_1$ and the incandescent light signal $S_A$ are then respectively held by the peak hold circuits 3 and 4.

A threshold value is set in advance to the threshold value comparison circuit 7 illustrated in FIG. 1. As illustrated in FIG. 1, the threshold value comparison circuit 7 compares the scattered light signal $S_1$ as obtained from the first peak hold circuit 3 to the threshold value. As illustrated in FIG. 2, in this case the scattered light signal $S_1$ is less than the threshold value, and therefore the AD converters 5 and 6 do not perform the AD conversion process. Moreover, the reset circuits 10 and 11 do not output reset signals to the peak hold circuits 3 and 4, and as illustrated in FIG. 2, the peak values $L_1$ and $L_A$ remain stored as-is.

Next, assume that as illustrated in FIG. 2, a scattered light signal $S_2$ and an incandescent light signal $S_B$ are obtained during the next particle detection event. As illustrated in FIG. 2, in this case the scattered light signal $S_2$ is greater than the threshold value, and therefore this event is treated as a true particle detection event. The threshold value comparison circuit 7 sends a reset signal to the second peak hold circuit 4 in order to reset the second peak hold circuit 4. It is preferable that this reset be performed at substantially the same time as it is detected that the scattered light signal $S_2$ is greater than the threshold value. However, as illustrated in FIG. 2, the incandescent light signal $S_B$ is obtained slightly after the scattered light signal $S_2$, and therefore the reset may be performed after a small time lag equal in duration to this delay.

As illustrated in the "Incandescent light peak hold reset" timing chart in FIG. 2, a reset signal is output once the scattered light signal $S_2$ exceeds the threshold value, thereby resetting the currently stored incandescent light peak value $L_A$.

As illustrated in FIG. 2, after the reset, the second peak hold circuit 4 holds the peak value of the new incandescent light signal $S_B$ and stores this value as the peak value $L_B$. Moreover, the first peak hold circuit 3 holds the peak value of the new scattered light signal $S_2$ and stores this value as the peak value $L_2$.

Furthermore, as illustrated in FIG. 2, after a prescribed period of time T elapses, the AD converters 5 and 6 convert the (analog) peak values $L_2$ and $L_B$ from the peak hold circuits 3 and 4 to digital values and outputs those digital values to the CPU 8. At the same time, the reset circuits 10 and 11 output reset signals to the peak hold circuits 3 and 4 (see the "Scattered light peak hold reset" and "Incandescent light peak hold reset" charts in FIG. 2) in order to reset the peak hold circuits 3 and 4. Note that the prescribed period of time T from once it is detected that the scattered light signal $S_2$ is greater than the threshold value until when the AD conversion process is implemented provides a delay that allows the scattered light signal $S_2$ and the incandescent light signal $S_B$ to reach their respective peak values.

A table that defines the correspondence between particle size and the intensity of the scattered light and the incandescent light is stored in advance in the particle size setting circuit 9. The CPU 8 illustrated in FIG. 1 converts the digital values from the AD converters 5 and 6 to particle sizes according to this correspondence table. Then, the calculated particle sizes are displayed on a display device 12 or the like. Moreover, multiplying the particle sizes by an appropriate density makes it possible to calculate the mass concentration per unit time as well. Furthermore, the number of particles for which the intensity of the resulting scattered light was greater than the threshold value can be detected. In this way, after the prescribed period of time T elapses, the CPU (processing unit) 8 can calculate one or more of the number of particles, the particle size, and the particle mass from the intensity of the scattered light and the incandescent light produced thereby.

As described above, in the present embodiment, the threshold value comparison circuit 7 sends a reset signal to the second peak hold circuit 4 when the signal from the first peak hold circuit 3 is greater than the threshold value. Therefore, the present embodiment makes it possible to accurately detect particles even when using a relatively simple signal processing scheme that utilizes the peak hold circuits 3 and 4 without losing the unique correspondence between individual particles and the resulting scattered light and incandescent light signals and without overestimating the number of particles.

INDUSTRIAL APPLICABILITY

The particle detection device of the present invention makes it possible to accurately detect particles and can be used to effectively measure the number, size, and mass concentration of particles contained in gases such as the atmosphere or the air in a cleanroom.

It will be apparent to those skilled in the art that various modifications and variations can be made in the present invention without departing from the spirit or scope of the invention. Thus, it is intended that the present invention cover modifications and variations that come within the scope of the appended claims and their equivalents. In particular, it is explicitly contemplated that any part or whole of any two or more of the embodiments and their modifications described above can be combined and regarded within the scope of the present invention.

What is claimed is:

1. A particle detector, comprising:
   a scattered light detector that detects an intensity of light scattered by a particle as a result of being irradiated with a laser beam;
   an incandescent light detector that detects an intensity of incandescent light generated by said particle as a result of being irradiated with said laser beam; and
   a signal processing part that includes:
      a first peak hold circuit that holds a peak value in the intensity of the light scattered by said particle detected by the scattered light detector;
      a second peak hold circuit that holds a peak value in the intensity of the incandescent light generated by said particle detected by the incandescent light detector; and
      a threshold value comparison circuit that compares the peak value held by the first peak hold circuit to a prescribed threshold value and, when the peak value held by the first peak hold circuit exceeds the prescribed threshold value, outputs a reset signal to the second peak hold circuit immediately thereafter so that the peak value previously held by the second peak hold circuit is reset immediately after the peak value held by the first peak hold circuit exceeds the prescribed threshold value,
   wherein said signal processing part is configured such that after a prescribed time has passed since when the peak value held by the first peak hold circuit is determined to exceed the prescribed threshold value, the respective peak values then held by the first and second peak hold circuits are both reset.

2. A particle detector, comprising:
   a scattered light detector that detects an intensity of light scattered by a particle as a result of being irradiated with a laser beam;
   an incandescent light detector that detects an intensity of incandescent light generated by said particle as a result of being irradiated with said laser beam; and
   a signal processing part that includes:
      a first peak hold circuit that holds a peak value in the intensity of the light scattered by said particle detected by the scattered light detector;
      a second peak hold circuit that holds a peak value in the intensity of the incandescent light generated by said particle detected by the incandescent light detector; and
      a threshold value comparison circuit that compares the peak value held by the first peak hold circuit to a prescribed threshold value and, when the peak value held by the first peak hold circuit exceeds the prescribed threshold value, outputs a reset signal to the second peak hold circuit immediately thereafter so that the peak value previously held by the second peak hold circuit is reset immediately after the peak value held by the first peak hold circuit exceeds the prescribed threshold value,
   wherein the signal processing part further includes:
      an analogue-digital (AD) conversion circuit or circuits that convert the peak values held by the first and second peak hold circuits to respective digital signals after a prescribed time has passed since when the peak value held by the first peak hold circuit is determined to exceed the prescribed threshold value, and wherein said signal processing part is configured such that after another prescribed time that is longer than said prescribed time has passed since when the peak a held by the first peak hold circuit is determined to exceed the prescribed threshold value, the respective peak values then held by the first and second peak hold circuits are both reset.

* * * * *

UNITED STATES PATENT AND TRADEMARK OFFICE
CERTIFICATE OF CORRECTION

PATENT NO. : 9,851,292 B2
APPLICATION NO. : 15/177593
DATED : December 26, 2017
INVENTOR(S) : Masaya Tabaru et al.

Page 1 of 1

It is certified that error appears in the above-identified patent and that said Letters Patent is hereby corrected as shown below:

In the Claims

Column 9, Line 8, the text "the peak a held" should be changed to -- the peak value held --.

Signed and Sealed this
Twelfth Day of June, 2018

Andrei Iancu
*Director of the United States Patent and Trademark Office*